United States Patent [19]

Ihm et al.

[11] Patent Number: 6,063,943

[45] Date of Patent: May 16, 2000

[54] POLYIMIDE-SUPPORTED TRANSITION METAL COMPLEX CATALYST AND PROCESS FOR PREPARING EPOXY COMPOUNDS USING THE SAME

[75] Inventors: Son Ki Ihm, Seoul; Chang Gun Oh, Kyungsangnam-do; Jou Hyeon Ahn, Kyungsangnam-do; Jong Chan Kim, Kyungsangnam-do, all of Rep. of Korea; David C. Sherrington, Glasgow, United Kingdom

[73] Assignee: Korea Advanced Institute of Science and Technology, Rep. of Korea

[21] Appl. No.: 09/209,535

[22] Filed: Dec. 11, 1998

[30] Foreign Application Priority Data

Dec. 11, 1997 [KR] Rep. of Korea ........................ 97-67965

[51] Int. Cl.[7] ........................ C07D 301/12; C07D 301/19

[52] U.S. Cl. .......................... 549/525; 549/529; 549/530; 549/531; 549/533

[58] Field of Search ..................................... 549/525, 529, 549/530, 531, 533

[56] References Cited

U.S. PATENT DOCUMENTS

| | | | |
|---|---|---|---|
| 5,633,391 | 5/1997 | Fenelli | 549/525 |
| 5,663,384 | 9/1997 | Shum et al. | 549/529 |
| 5,670,674 | 9/1997 | Grey | 549/533 |

*Primary Examiner*—Ba K. Trinh
*Attorney, Agent, or Firm*—Knobbe, Martens, Olson & Bear, LLP

[57] ABSTRACT

The present invention relates to a heterogeneous polyimide-supported transition metal complex catalyst for epoxidation of olefin, which is prepared by impregnating a heat- and acid-resistant polyimide resin with a homogeneous metal catalyst of molybdenum, vanadium, tungsten or titanium, and a process for preparing epoxy compounds using the same. The heterogeneous polyimide-supported transition metal complex catalyst of the invention provides superior catalytic activity, selectivity and stability in the epoxidation of higher olefin. Further, the catalyst of the invention has strong resistance against heat and acid. Besides, the catalyst of the invention may provide the following advantages which are critical in industrial use: it permits relatively high yield of epoxy compounds; and, it can be easily separated from the reaction product, which eases recycling of the catalyst.

11 Claims, 1 Drawing Sheet

POLYIMIDE-SUPPORTED TRANSITION METAL COMPLEX CATALYST AND PROCESS FOR PREPARING EPOXY COMPOUNDS USING THE SAME

FIELD OF THE INVENTION

The present invention relates to a polyimide-supported transition metal complex catalyst and a process for preparing epoxy compounds, more specifically, to a heterogeneous polyimide-supported transition metal complex catalyst for epoxidation of olefin, which is prepared by impregnating a heat- and acid-resistant polyimide resin with a homogeneous metal catalyst of molybdenum, vanadium, tungsten or titanium, and a process for preparing epoxy compounds using the same.

BACKGROUND OF THE INVENTION

Epoxidation of olefin compounds, like epoxidation of propylene to give propylene oxide, has been well known in the art, where an oxygen-donating agent of alkyl hydroperoxide and a homogeneous molybdenum catalyst or a heterogeneous titanium/silica catalyst are essentially required.

Sherrington and Simpson-discloses a supported metal catalyst by impregnating polystyrene resin with molybdenum and vanadium catalyst(see: Sherrington D. C. and Simpson S., Journal of Catalysis, 131:115–126, 1991). Miller and Sherrington also teaches a molybdenum(VI) catalyst impregnated in a heat-resistant polymer of polybenzimidazole which is employed in the epoxidation of cyclohexene(see: Miller M. and Sherrington D. C., Journal of Catalysis, 152:377–383, 1995).

Comparative study on the said two catalysts has revealed that: the catalyst impregnated in a heat-resistant polymer of polybenzimidazole has a catalytic activity and stability better than that of polystyrene-supported catalyst; and, the stability of the said two catalysts significantly decreases in the epoxidation of higher olefins.

In addition, U.S. Pat. No. 5,420,313 discloses an epoxidation of olefin by a molybdenum catalyst impregnated in polybenzimidazole resin, where the catalyst showed excellent catalytic activity and selectivity in the course of preparing propylene oxide from propylene, and retained catalytic activity on recycling without leaching. The catalyst, however, has revealed several shortcomings as follows: First, its catalytic activity decreased gradually, when it is recycled in the epoxidation of a higher olefin such as cyclohexene; Secondly, the polybenzinidazole resin employed as a support can only be prepared by a complicate melting process at a high temperature over 200° C.; Thirdly, the monomer used for preparing the polybenzimidazole resin is very expensive.

Therefore, there are strong reasons for developing a novel supported catalyst which has a high catalytic activity and selectivity in the epoxidation of higher olefin and retains its activity after repeated use, by employing an inexpensive heat-resistant polymer support.

SUMMARY OF THE INVENTION

In accordance with the present invention, the inventors have prepared a heterogeneous metal catalyst for epoxidation of olefin, by impregnating a heat- and acid-resistant polyimide resin obtained by condensation polymerization of dianhydride and diamine with a homogeneous catalyst such as molybdenum, vanadium, tungsten or titanium. The heterogeneous epoxidation catalyst of the invention provides a superior catalytic activity, selectivity and stability, which eases the epoxidation of higher olefin by peroxide.

A primary object of the present invention is, therefore, to provide a polyimide-supported transition metal complex catalyst for the epoxidation of olefin.

The other object of the invention is to provide a process for preparing epoxy compounds from olefin using the catalyst.

DETAILED DESCRIPTION OF THE INVENTION

Figure 1:
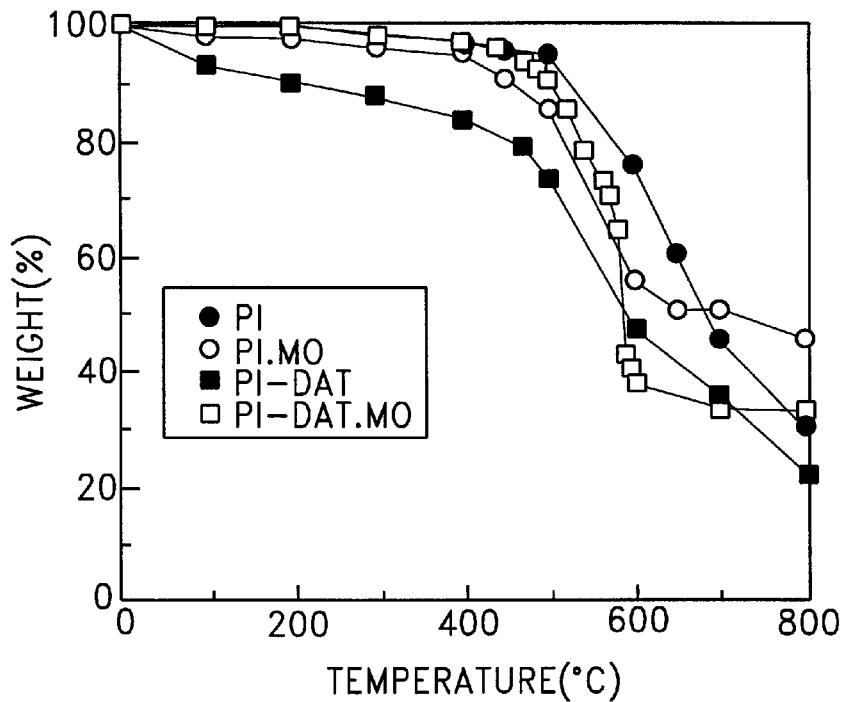
FIG. 1 is a graph showing the result of thermal gravimetric-analysis(TGA) analysis of spherical polyimide paricle and molybdenum catalyst impregnated in the particle.

In accordance with the present invention, a poly4.mide resin particle as a support is first prepared by condensation polymerization of dianhydride and diamine, preferably in a spherical shape for the convenience of handling. For example, a polyimide resin particle having the chemical formula (I) is prepared from pyromellitic dianhydride and 1,4-phenylenediamine.

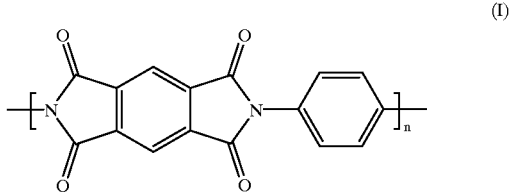

(I)

Although the polyimide resin particle has no functional group which is bonded to a metal component, imperfect formation of an imide ring during condensation leaves a carboxyl croup to be involved in a chemical bond with the metal component. Further, functional polyimide resin particle (II) is prepared by using diamine containing a functional group such as triazole, carboxyl, sulfonyl, pyridine and hydroxyl group which can be involved in the chemical bond with the metal component.

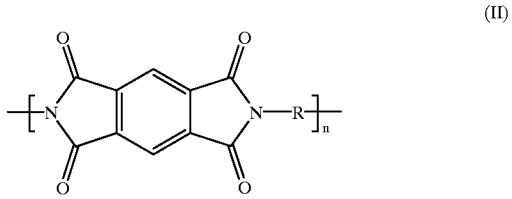

(II)

In this connection, the diamine includes materials containing two or more amine groups such as 1,4-phenylenediamine, 3,5-diamino-1,2,4-triazole, 3,5-diaminobenzenesulfonic acid, 3,5-diaminobenzoic acid, 2,6-diaminopyridine, 1,3-diamino-2-hydroxypropane, diaminomaleonitrile, 2,6-diaminoanthraquinone and 3,3'-diamino-4 4'-dihydroxybiphenyl.

Further, the dianhydride includes materials containing two or more anhydryl groups such as 1,2,4,5-benzene tetracarboxylic dianhydride and 3,3',4,4'-benzophenonetetracarboxylic dianhydride.

The heterogeneous polyimide-supported catalyst of the invention is prepared by impregnating the polyimide resin particle prepared as above with a homogeneous organic metal complex catalyst such as molybdenum, vanadium, tungsten and titanium, most preferably molybdenum, and making a chemical bond between the functional group of the polyimide support and the metal catalyst thereby. In this connection, one or two kinds of metal catalysts may be impregnated in one polyimide support.

In the heterogeneous polyimide-supported metal complex catalyst of the invention, content of the functional group of support which may be involved in chemical bonds with the metal component ranges from 0.1 mmol/g to 4 mmol/g, preferably 0.2 mmol/g to 2.5 mmol/g, and content of the metal component ranges from. 0.1 mmol/g to 5 mmol/g, preferably 0.1 mmol/g 2 mmol/g. In addition, the molar ratio of the functional group of support to the metal component ranges from 1:1 to 15:1, preferably 1:1 to 10:1.

On the other hand, the heterogeneous polyimide-supported metal complex catalyst may be activated either by an appropriate peroxide prior to use or by a peroxide which is included in the reaction mixture in the course of epoxidation.

In accordance with the present invention, the epoxy compounds are prepared by reacting a peroxide and an olefin compound in a molar ratio of 1:0.5 to 1:100, preferably 1:1 to 1:50, by employing the heterogeneous polyimide-supported metal complex catalyst, where the molar ratio of the catalyst and the peroxide ranges from 0.00001:1 to 1:1, preferably 0.002:1 to 0.03:1.

Preferably, organic olefin compounds with at least one double bond are employed in a form of linear, branched or ring. Further, the olefin compounds may have one or more acryl ring. The olefin compound may be a conjugate or not, in case of having two or more double bonds. The olefin compounds may also have aryl hydroxy, aryl chlorine, aryl ether or aryl ester substituent. The olefin compounds include vinyl ester, phenyl and nitrile compounds. Preferably, the olefin compounds may be substituted with electron-donating groups. However, if they have a substituent of an electron-withdrawing group like nitrile, the substituent should not be placed at a double bond of them, but should be far from the double bond. The olefin compounds are represented as the general formula (III):

R—CH=CH—R'  (III)

wherein, R and R' are same or similar compounds, and carbon number less than 30 is preferred; and, when R and R' are ring compounds, carbon number of less than 10 is preferred. One or both of R and R' may have aryl hydroxy, aryl chlorine, aryl ether or aryl ester substituent. Additionally, one or both of R and R' may have vinyl ester, nitrile or phenyl substituent.

Preferably, the olefin compounds are ethylene, propylene and/or butene, for example, olefins such as 1-butene, cis or trans 2-butene, pentene, hexene, octene, decene, cyclohexene, 4-vinyl-cyclohexene, unsaturated glycerin ester, arylchloride, styrene, methylene hexane, cyclopentadiene, butadiene, etc., may be employed in the preparation or epoxy compound as a single compound or a mixture thereof. In addition to the olefin compounds, small quantities of impurities like alkanes, aromatic compounds, alcohols, ethers and acids may be further added in the preparation of epoxy compound.

Preferably, peroxides such as hydrogen peroxide, organic peroxides like alkyl hydroperoxide, peroxide ether or peracid are employed in the epoxidation of olefin, though tert-butyl hydroperoxide, cumene hydroperoxide, ethylbenzene hydroperoxide or hydrogen peroxide are more preferred.

In carrying out the epoxidation of olefin, in addition to the reactants, aromatic or aliphatic alcohols, alkanes, esters and ketones, and chlorine solvents like 1,2-dichloroethane may be added as a solvent, where the solution may include a little amount of water, though no water condition is most preferred.

In accordance with the present invention, the epoxidazion of olefin may be carried out under an atmospheric or high pressure. In case that olefin compounds are gas state under an atmospheric pressure, the epoxidation reaction should be carried out under a high pressure so that it can be done in liquid phase. For example, in the epoxidation of propylene, the pressure should be elevated up to 100 bar, where inert gas like nitrogen, helium, air or alkane may be employed to keep the pressure high. The temperature condition may be varied depending on the kind of reactant, though a temperature from 20° C. to 500° C. is preferred. The epoxidation may be carried out in batch-type or continuous process, though the continuous process is more preferable.

The present invention is further illustrated by the following examples, which should not to be taken to limit the scope of the invention.

EXAMPLE 1

Preparation of Polyimide Resin Particles

Example 1-1

Preparation of a Functional Group-Free Polyimide Resin Particle

A polyimide resin particle free of functional groups was prepared by condensing 1,4-phenylenediamine(PDA) and pyromellitic dianhydride(PMDA): To a 250 ml of 3-necked round-bottomed flask were added 5.4 g of PDA(0.050 mol) and 66.08 g of N,N'-dimethylacetamide(DMAc), and stirred under an environment $N_2$ until EDA was dissolved thoroughly. Then, 11.12 g of PMDA(0.052 mol) was slowly added in a small quantity, while keeping the reaction temperature low with a cold water bath. As the solution became transparent, the viscosity of the solution was increased. After stirring for about 2 hours, the solution was stored under an environment of N.

And then, to a condensing reactor including a suspension stabilizer were added 500 g of paraffin oil and 240.38 g of poly(amic acid)(FAA) solution(20%(w/v) PAA in DMAc), and stirred at 400 rpm under an environment of $N_2$. In this connection, poly(maleic anhydride-co-octadec-l-ene)(1:1) or ICI polymeric dispersant was used as a suspension stabilizer. After stirring at 60° C. for about 2 hours, a mixture of acetic anhydride(35.73 g, 0.35 mol) which is a dehydrating agent and pyridine(23.73 g, 0.30 mol) was added in a small quantity over 1 hour. After dehydration for 24 hours with constant stirring, a polyimide was obtained and dried in a vacuum dry oven(80° C.) for 24 hours.

Example 1-2

Preparation of a Polyimide Resin Particle Possessing Functional Group

A polyimide resin particle with a functional group was prepared by condensing a diamine having functional groups and a dianhydride, that is, condensation polymerization of 3,5-diaminobenzenesulfonic acid and pyromellitic dianhydride(PMDA) was carried out in an analogous manner as in Example 1-1. The polyimide resin particle thus prepared was spherical and had a functional group of sulfonyl group(—$SO_3H$).

Then, to prepare a heat-resistant polymer support suitable for practical use, a cross-liking agent was used to modify the internal structure of the polyimide resin particle, in accordance with the cross-liking technique which is widely used for preparing a polystyrene support. For example, a desired amount of cross-liking agent possessing more than 3 amine groups was substituted for diamine in order to prepare a cross-linked polyimide resin particle, where commercially available tris(2-aminoethyl)amine and melamine, and 3,3'5, 5'-tetraamino-benzophenone were employed as the cross-linking agents.

EXAMPLE 2

Example 2-1

Preparation of a Polyimide-Supported Catalyst

Polyimide-supported transition metal complex catalyst was prepared as follows: To a 50 ml of round-bottomed flask were added 2.0 g of polyimide particle(PI-DAT) possessing a functional group and 7.0 g of a homogeneous organic metal complex, i.e., molybdenyl acetylacetonate($MoO_2$ $(acac)_2$), and 20 ml of ethanol was further added. The reaction mixture was kept under a reflux for 3 days. Then, filtration or the reaction mixture was carried out to obtain a polymer particle impregnated with the metal catalyst and subsequently washed with toluene, extracted with ethanol by the aid of Soxhlet, and dried in a vacuum dry oven(80° C.).

The amount of the catalyst component impregnated in the polymer was measured as follows: 0.02 g or polymer-impregnated metal complex was placed in a silica melting pot, and 1 g or $KNO_3$ and 2 ml of aqua regia were added as oxidants. Metal complex-free samples comprising only 1 g of $KNO_3$ and 2 ml of aqua regia were prepared in a similar manner. Then, the melting pot was placed in a furnace and temperature was gradually elevated to 420° C. The melting pot was left to stand for 3–4 hours at a temperature of 420° C. After cooling to a room temperature, the residue in the pot was completely solubilized by the addition of 50 ml of aqua regia. Then, the solution was placed in a 50 ml volumetric flask and diluted with water to reach the total volume of 50 ml.

The metal content in the solution was measured by the aid of atomic absorption spectrometer and inductively coupled plasma(ICP) spectrometer. A standard solution for measurement was prepared as follows: For measuring Mo content by atomic absorption spectrometer, standard solutions of 50, 75, 100, and 200 ppm Mo were prepared by diluting a commercially available 100 ppm Mo solution with a blank solution, and the other was used as blank. For measuring Mo content by inductively coupled plasma(ICP) spectrometer, standard solutions of 10 ppm and samples of less than 10 ppm were prepared. Based on the method described above, PI-DAT.Mo(metal catalyst impregnated in a polyimide possessing a triazol group) was found to have a metal content of 0.86 mmolMo/g. Other PI-DAT.Mo(metal catalyst impregnated in a polyimide possessing a carboxyl group) prepared as described above was found to have a metal content of 1.30 mmolMo/g. Mo contents of these impregnated catalysts were adjusted to have the same value when used in an epoxidation reaction.

These impregnated catalysts were activated for later use, by reflux in 10 ml of toluene containing 5 mmol of tert-butyl-hydroperoxide(TBHP) (hereinafter referred to as "TBHP(5 mmol)/toluene" for convenience) until the color of the catalysts turned to a bright yellow color.

Figure 2:
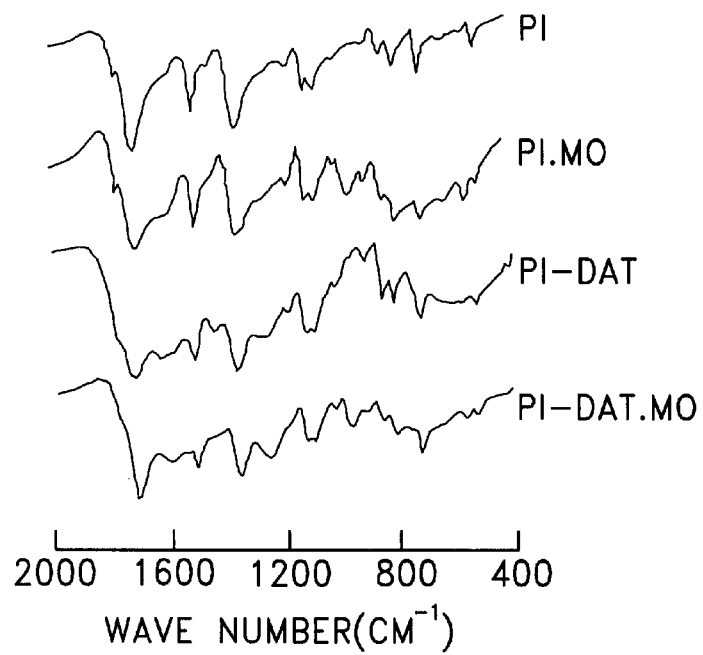
FIG. 2 is a Fourier transform IR spectra of the spherical polyimide paricle and molybdenum catalyst impregnated in the particle.

FIG. 1 shows the results of the thermal gravimetric analyses of spherical polyimide particle and polyimide-supported molybdenum catalysts prepared in Examples 1 and the 2-1, respectively. FIG. 2 shows the Fourier transform IR spectra of them. In FIGS. 1 and 2, the symbols used are: PI, polyimide particle; PI.Mo, Mo catalyst impregnated in polyimide free of functional group; PI-DAT, polyimide possessing a functional group; and, PI-DAT.Mo, Mo catalyst impregnated in polyimide possessing a functional group.

Example 2-2

Epoxidation of Cyclohexene

A peroxide to be used in the epoxidation was prepared in a form of anhydrous TBHP in toluene as follows: 60 ml of 70% TBHP solution and 80 ml of toluene were placed in a 250 ml separating funnel, stirred gently for about 1 minute. After phase separation was accomplished, the lower water phase was discarded and water was removed from the upper phase by the aid of trap. That is, the upper phase solution and boiling chips were placed in a round-bottomed flask fitted with a reflux condenser. After reflux for 1 hour, 4 ml of water and excessive toluene were distilled and passed through a branch. 1 hour later, 2 ml of water and toluene were distilled out and for another 1 hour, only toluene was distilled out TBHP/toluene was placed in a flask together with 5 A molecular sieve and stored in a refrigerator. The concentration of TBHP thus prepared was measured by iodide method.

A 3-necked reactor was used in the epoxidation of cyclohexene, and thermostatic circulating water bath was employed for controlling the reaction temperature precisely. Under an environment of $N_2$, 0.08 g of polyimide-supported metal catalyst, 7.5 ml of cyclohexene (74 mmol), and 0.5 ml of o-dichlorobenzene(an internal standard of gas chromatography) were placed in a reactor fitted with a shaker, sampler and a condenser, and stirred at 60° C. for 20 min to reach a thermal equilibrium. Then, 1.4 to 1.5 ml of anhydrous TBHP(5 mmol)/toluene prepared as above was added to initiate the reaction. The product was collected and its concentration was determined by gas chromatography, whose analysis condition was as follows:

Gas chromatograph: HP 5890 II Plus

Column: Ultra 2 (Crosslinked 5% Ph Me Silicone)
 Length: 25 mm
 Inside diameter: 0.22 mm
 Film thickness: 0.52 µm Oven temperature: 60° C. (5 min)→120° C. (30° C./min)

Inflector: 250° C.

Detector: 270° C. (FID)

Carrier Gas: Helium 1 ml/min

The yield of epoxide was defined as 100% when all of the oxygen atoms of an oxygen donating agent included in a reaction mixture participate in the epoxidation of olefin compound.

The amount of catalyst separated from the polyimide resin in the course of the epoxidation reaction was measured. After the reaction was completed, the catalyst thus separated was filtrated and washed thoroughly, and the inside of reactor was also washed thoroughly. The resultant solution was collected and applied to a rotating evaporator to remove solvent finally, to give bright yellow residues. The residues were dissolved in aqua regia for about 48 hours, diluted with distilled water, and then analyzed by the aid of atomic absorption spectrometer or inductively coupled plasma(ICP) spectrometer.

EXAMPLE 3

Effect of the Activation of Catalyst on the Yield of Epoxidation

Epoxidation of cyclohexene was carried out at 80° C. analogously as in Example 2-2 by employing a Mo catalyst impregnated in polyimide possessing triazole group. Before used in epoxidation, the catalyst was activated for a period by employing the TBHP(5 mmol)/toluene prepared in Example 2-2. The yields of cyclohexene oxide(%) depending on the degree of activation of the catalyst and reaction time were investigated by the aid of a gas chromatography, which were summarized in Table 1 below.

TABLE 1

The yield of cyclohexene oxide produced by the epoxidation of cyclohexene depending on the degree of activation of a catalyst (unit: %)

| Reaction time (min) | Non-activated | Activated for 12 hrs | Activated for 24 hrs | Activated for 48 hrs |
| --- | --- | --- | --- | --- |
| 20 | 93.5 | 64.1 | 2.5 | 4.0 |
| 40 | 100 | 92.6 | 18.9 | 27.6 |
| 60 | 100 | 100 | 61.4 | 77.2 |
| 80 | 100 | 100 | 85.8 | 95.0 |
| 100 | 100 | 100 | 100 | 100 |
| 120 | 100 | 100 | 100 | 100 |

EXAMPLE 4

The stability of catalyst was investigated in 10 to 12 times of experiments using a recyclable Mo catalyst impregnated in polyimide possessing triazole group(PI-DAT.Mo) while varying the reaction time in an analogous manner as in Example 3. Amount of metal separated from the polyimide-supported catalyst was measured in each experiment. At the end of reaction, the separated catalyst was isolated from the reaction mixture by filtration, washed with acetone, and dried for later use. The yields of cyclohexene oxide(%) produced by the epoxidation of cyclohexene using the catalysts activated for 0, 12, 24 and 48 hrs were determined, which were disclosed in Tables 2, 3, 4 and 5 below, respectively.

TABLE 2

The yield of cyclohexene oxide produced by the epoxidation of cyclohexene using a non-activated PI-DAT.Mo catalyst (unit: %)

| Experiment No. | Reaction time | | | | | |
| --- | --- | --- | --- | --- | --- | --- |
| | 20 min | 40 min | 60 min | 80 min | 100 min | 120 min |
| 1 | 93.5 | 100 | 100 | 100 | 100 | 100 |
| 2 | 86.3 | 99.4 | 100 | 100 | 100 | 100 |
| 3 | 47.5 | 91.9 | 100 | 100 | 100 | 100 |
| 4 | 64.5 | 95.5 | 100 | 100 | 100 | 100 |
| 5 | 68.6 | 94.6 | 100 | 100 | 100 | 100 |
| 6 | 4.9 | 29.8 | 82.1 | 98.6 | 100 | 100 |
| 7 | 3.0 | 6.0 | 60.4 | 93.2 | 100 | 100 |
| 8 | 53.5 | 88.2 | 97.5 | 100 | 100 | 100 |

TABLE 2-continued

The yield of cyclohexene oxide produced by the epoxidation of cyclohexene using a non-activated PI-DAT.Mo catalyst (unit: %)

| Experiment No. | Reaction time | | | | | |
| --- | --- | --- | --- | --- | --- | --- |
| | 20 min | 40 min | 60 min | 80 min | 100 min | 120 min |
| 9 | 2.6 | 2.6 | 3.4 | 23.2 | 75.7 | 100 |
| 10 | 66.3 | 91.9 | 100 | 100 | 100 | 100 |
| 11 | 45.3 | 71.1 | 87.0 | 95.7 | 100 | 100 |
| 12 | 38.3 | 71.8 | 80.1 | 95.4 | 100 | 100 |

TABLE 3

The yield of cyclohexene oxide produced by the epoxidation of cyclohexene using a PI-DAT.Mo catalyst activated for 12 hrs (unit: %)

| Experiment No. | Reaction time | | | | | |
| --- | --- | --- | --- | --- | --- | --- |
| | 20 min | 40 min | 60 min | 80 min | 100 min | 120 min |
| 1 | 64.1 | 92.6 | 100 | 100 | 100 | 100 |
| 2 | 60.0 | 91.7 | 100 | 100 | 100 | 100 |
| 3 | 75.4 | 97.8 | 100 | 100 | 100 | 100 |
| 4 | 32.0 | 66.9 | 82.5 | 94.7 | 100 | 100 |
| 5 | 29.0 | 50.1 | 82.6 | 94.2 | 100 | 100 |
| 6 | 17.7 | 49.7 | 71.0 | 90.1 | 97.9 | 100 |
| 7 | 10.8 | 30.0 | 67.2 | 87.2 | 95.9 | 100 |
| 8 | 7.7 | 19.3 | 55.9 | 81.3 | 93.6 | 100 |
| 9 | 27.0 | 60.0 | 78.5 | 88.8 | 96.0 | 100 |
| 10 | 0 | 4.40 | 11.3 | 34.6 | 63.3 | 82.6 |

TABLE 4

The yield of cyclohexene oxide produced by the epoxidation of cyclohexene using a PI-DAT.Mo catalyst activated for 24 hrs (unit: %)

| Experiment No. | Reaction time | | | | | |
| --- | --- | --- | --- | --- | --- | --- |
| | 20 min | 40 min | 60 min | 80 min | 100 min | 120 min |
| 1 | 18.9 | 61.4 | 85.8 | 100 | 100 | 100 |
| 2 | 32.8 | 74.3 | 100 | 100 | 100 | 100 |
| 3 | 4.2 | 9.6 | 53.4 | 80.3 | 95.6 | 100 |
| 4 | 0 | 4.2 | 22.4 | 69.1 | 90.5 | 95.9 |
| 5 | 0 | 3.4 | 6.9 | 40.9 | 87.9 | 93.15 |
| 6 | 0 | 3.3 | 4.2 | 18.3 | 45.2 | 66.7 |
| 7 | 0 | 2.9 | 8.4 | 18.3 | 42.1 | 62.9 |
| 8 | 0 | 3.0 | 3.9 | 20.1 | 47.6 | 70.7 |
| 9 | 0 | 2.7 | 4.2 | 8.2 | 49.3 | 60.4 |
| 10 | 0 | 0 | 2.5 | 5.3 | 20.2 | 28.1 |

TABLE 5

The yield of cyclohexene oxide produced by the epoxidation of cyclohexene using a PI-DAT.Mo catalyst activated for 48 hrs (unit: %)

| Experiment No. | Reaction time | | | | | |
| --- | --- | --- | --- | --- | --- | --- |
| | 20 min | 40 min | 60 min | 80 min | 100 min | 120 min |
| 1 | 24.8 | 93.3 | 97.7 | 100 | 100 | 100 |
| 2 | 5.0 | 65.3 | 89.2 | 100 | 100 | 100 |
| 3 | 4.8 | 16.5 | 73.8 | 96.7 | 100 | 100 |
| 4 | 5.3 | 25.3 | 61.3 | 83.6 | 95.5 | 100 |
| 5 | 0 | 3.9 | 25.8 | 72.0 | 90.8 | 100 |
| 6 | 3.5 | 9.7 | 50.2 | 80.7 | 94.8 | 100 |
| 7 | 0 | 0 | 5.8 | 34.8 | 69.0 | 88.4 |

TABLE 5-continued

The yield of cyclohexene oxide produced by the epoxidation of cyclohexene using a PI-DAT.Mo catalyst activated for 48 hrs (unit: %)

| Experiment No. | Reaction time | | | | | |
|---|---|---|---|---|---|---|
| | 20 min | 40 min | 60 min | 80 min | 100 min | 120 min |
| 8 | 2.7 | 3.6 | 5.5 | 28.8 | 65.1 | 81.1 |
| 9 | 0 | 0 | 4.9 | 19.4 | 54.6 | 75.6 |
| 10 | 0 | 5.0 | 17.6 | 40.5 | 58.0 | 75.2 |

EXAMPLE 5

To investigate the effect of temperature on epoxidation using nonactivated PI-DAT.Mo catalyst(Mo catalyst impregnated in polyimide possessing triazol group), epoxidation of cyclohexene was carried out while varying the reaction temperature, and the yields of cyclohexene oxide(%) produced by the epoxidation of cyclohexene were determined, which were summarized in Table 6 below.

TABLE 6

The yield of cyclohexene oxide produced by the epoxidation of cyclohexene using a nonactivated PI-DAT.Mo catalyst (unit: %)

| Reaction time (min) | Reaction temperature | | | | |
|---|---|---|---|---|---|
| | 60° C. | 65° C. | 70° C. | 75° C. | 80° C. |
| 20 | 6.8 | 7.0 | 35.4 | 90.0 | 93.5 |
| 40 | 10.4 | 59.6 | 83.6 | 100 | 100 |
| 60 | 16.8 | 81.4 | 95.4 | 100 | 100 |
| 80 | 42.0 | 86.0 | 98.0 | 100 | 100 |
| 100 | 63.0 | 94.0 | 100 | 100 | 100 |
| 120 | 87.4 | 100 | 100 | 100 | 100 |

EXAMPLE 6

Example 6-1

Preparation of a Mo Catalyst Impregnated in Cross-linked Polyimide Resin Possessing Triazole Group Using 3,5-diamino-1,2,4-triazole as a diamine, pyromellitic dianhydride(PMDA) as a dianhydride, and Tris(2-aminoethyl)amine as a cross-linking agent, a polyimide resin possessing triazole group was prepared and impregnated with $MoO_2(acac)_2$ to give a polyimide-supported Mo catalyst as follows: 8.99 g($9 \times 10^{-2}$ mol) of 3,5-diamino-1,2,4-triazole and 114.0 g of N,N'-dimethyl-acetamide(DMAc) were placed in 1000 ml 4-cylindrical reactor and stirred under an environment of $N_2$ to dissolve the diamine thoroughly. And then, 22.4462 g($13.5 \times 10^{-2}$ mol) of PMDA was added in a small quantity and reacted at room temperature for 24 hour. To the reactor was added 450 g of paraffin oil including a suspension stabilizer, and stirred for about 2 hours. Subsequently, Tris(2-aminoethyl)amine, a cross-linking agent was added in a small quantity and reacted for 24 hours to give a suspension. To the suspension was added a mixture of a dehydrating agent, i.e., anhydride acetic acid(36.9 g, 0.36 mol) and pyridine (24.93 g, 0.32 mol) in a small quantity through 1 hour, and dehydrated for 24 hours with constant stirring to give a cross-linked polyimide particle. The polyimide thus prepared was filtrated, extracted in a Soxhlet for 24 hours with dichloromethane, and dried in a vacuum dry oven(80° C.) for 24 hours. Finally, transition metal complex catalyst impregnated in polyimide was prepared analogously as in Example 2-1, and the metal content was determined to be 0.92 mmol/g.

Example 6-2

Epoxidation of Cyclohexene

Epoxidation of cyclohexene oxide was carried out by employing the Mo catalyst impregnated in the cross-linked polyimide possessing triazole group, in an analogous manner as in Example 4 with an exception that the reaction was carried out at a temperature of 70° C. Then, the yields of cyclohexene oxide(%) produced by the epoxidation of cyclohexene were determined, which were disclosed in Table 7 below.

TABLE 7

The yield of cyclohexene oxide produced by the epoxidation of cyclohexene using a nonactivated and cross-linked PI-DAT.Mo catalyst (unit: %)

| Experiment No. | Reaction time | | | | | |
|---|---|---|---|---|---|---|
| | 20 min | 40 min | 60 min | 80 min | 100 min | 120 min |
| 1 | 97.4 | 100 | 100 | 100 | 100 | 100 |
| 2 | 94.3 | 100 | 100 | 100 | 100 | 100 |
| 3 | 94.7 | 100 | 100 | 100 | 100 | 100 |
| 4 | 15.0 | 41.5 | 79.8 | 82.0 | 87.0 | 89.8 |
| 5 | 50.8 | 89.0 | 100 | 100 | 100 | 100 |
| 6 | 50.9 | 80.0 | 94.7 | 87.0 | 100 | 100 |
| 7 | 29.3 | 60.1 | 85.8 | 82.0 | 100 | 100 |
| 8 | 8.2 | 21.6 | 37.1 | 56.0 | 70.0 | 80.0 |
| 9 | 14.4 | 16.5 | 19.7 | 46.0 | 77.0 | 84.0 |
| 10 | 6.3 | 12.0 | 18.7 | 42.0 | 65.0 | 74.0 |

EXAMPLE 7

Example 7-1

Preparation of a Mo Catalyst Impregnated in Polyimide Resin Possessing Triazole Group A polyimide(PI(C=O)-DAT) possessing triazole group was synthesized analogously as in Example 1-2 except for employing 3,3',4,4'-benzophenonetetracarboxylic dianhydride as a dianhydride, and impregnated with Mo catalyst analogously as in Example 2-1, where the Mo catalyst content was to be 0–14 mmol/g.

Example 7-2

Epoxidation of Cyclohexene

Epoxidation of cyclohexene was carried out by employing the Mo catalyst impregnated in PI(C=O)-DAT analogously as in Example 4, with an exception that the reaction was carried out at a temperature of 60° C. Then, the yield of cyclohexene oxide(%) produced by the epoxidation of cyclohexene were determined, which were disclosed in Table 8 below.

TABLE 8

The yield of cyclohexene oxide produced by the epoxidation of cyclohexene using a PI(C = 0)-DAT.Mo catalyst (unit: %)

| Experiment | Reaction time | | | | | |
|---|---|---|---|---|---|---|
| No. | 20 min | 40 min | 60 min | 80 min | 100 min | 120 min |
| 1 | 55.3 | 78.0 | 89.4 | 92.0 | 100 | 100 |
| 2 | 60.2 | 89.0 | 95.0 | 100 | 100 | 100 |
| 3 | 50.5 | 74.6 | 92.2 | 93.2 | 86.6 | 100 |
| 4 | 32.5 | 54.5 | 69.1 | 75.0 | 86.0 | 91.2 |
| 5 | 35.6 | 60.2 | 73.1 | 79.3 | 86.5 | 95.0 |
| 6 | 15.2 | 30.8 | 43.3 | 56.0 | 63.3 | 69.0 |
| 7 | 15.0 | 32.3 | 49.1 | 55.8 | 65.8 | 72.8 |
| 8 | 10.3 | 17.8 | 23.0 | 24.0 | 35.8 | 40.5 |
| 9 | 13.4 | 25.3 | 36.5 | 40.6 | 52.0 | 58.2 |
| 10 | 14.3 | 26.3 | 36.3 | 42.9 | 53.2 | 56.4 |

EXAMPLE 8

Epoxidation or Cyclooctene

Epoxidation of cis-cyclooctene was carried out at 80° C. analogously as the epoxidation of cylcohexene, where the composition of reaction mixture was as below:

| | |
|---|---|
| cis-cyclooctene oxide | 56.7 mmol |
| Mo | $3.4 \times 10^{-2}$ mmol |
| tert-butyl-hydroperoxide | 5 mmol |
| ortho-dichlorobenzene | 0.5 ml |
| toluene | 0.62 ml |

Toluene was added to reach the total reaction volume of 10 ml. The reaction was repeated 10 times as in Example 4. Then, the yields of cis-cyclooctene oxide(%) produced by the epoxidation of cis-cyclooctene were determined, which were disclosed in Table 9 below.

TABLE 9

The yield of cyclohexene oxide produced by the epoxidation of cyclohexene using a non-activated PI-DAT.Mo catalyst (unit: %)

| Experiment | Reaction time | | | |
|---|---|---|---|---|
| No. | 20 min | 40 min | 60 min | 80 min |
| 1 | 94.0 | 100 | 100 | 100 |
| 2 | 90.8 | 100 | 100 | 100 |
| 3 | 93.3 | 100 | 100 | 100 |
| 4 | 84.3 | 100 | 100 | 100 |
| 5 | 59.7 | 89.0 | 100 | 100 |
| 6 | 46.0 | 71.8 | 88.6 | 100 |
| 7 | 50.8 | 82.6 | 100 | 100 |
| 8 | 65.5 | 92.3 | 100 | 100 |
| 9 | 68.9 | 89.1 | 100 | 100 |
| 10 | 64.9 | 90.1 | 100 | 100 |

EXAMPLE 9

Epoxidation of 1-octene

Epoxidation of 1-octene was carried out analogously as in Example 8, with an exception that the composition of reaction was as below:

| | |
|---|---|
| 1-octene | 48.7 mmol |
| Mo | $3.4 \times 10^{-2}$ mmol |
| tert-butyl-hydroperoxide | 5 mmol |
| ortho-dichlorobenzene | 0.5 ml |
| toluene | 0.62 ml |

Then, the yield of 1,2-epoxyoctene oxide(%) produced by the epoxidation of 1-octene were determined, which were disclosed in Table 10 below.

TABLE 10

The yield of 1,2-epoxyoctene oxide produced by the epoxidation of 1-octene using a non-activated PI-DAT.Mo catalyst (unit: %)

| Experiment | Reaction time | | | | | |
|---|---|---|---|---|---|---|
| No. | 20 min | 40 min | 60 min | 80 min | 100 min | 120 min |
| 1 | 13.9 | 35.6 | 61.4 | 72.6 | 78.8 | 86.9 |
| 2 | 4.9 | 12.5 | 25.3 | 35.1 | 43.7 | 63.1 |
| 3 | 3.4 | 7.5 | 13.8 | 20.6 | 25.7 | 37.9 |
| 4 | 3.0 | 6.5 | 11.2 | 18.9 | 27.6 | 32.2 |
| 5 | 0 | 5.3 | 12.2 | 18.6 | 28.4 | 31.9 |
| 6 | 2.3 | 4.7 | 6.5 | 9.8 | 13.3 | 17.1 |
| 7 | 4.2 | 10.4 | 17.5 | 23.4 | 29.8 | 40.2 |
| 8 | 1.9 | 3.1 | 6.4 | 8.7 | 13.0 | 18.4 |
| 9 | 0 | 1.8 | 4.1 | 5.2 | 7.6 | 13.4 |
| 10 | 0 | 0 | 2.1 | 3.2 | 4.4 | 6.1 |

EXAMPLE 10

Effect of the Activation of Catalyst on the Yield of Epoxidation

The functional group-free polyimide resin prepared in Example 1-1 was impregnated with Mo catalyst to give a polyimide-supported Mo catalyst(i.e., PI.Mo catalyst), where the Mo catalyst content was determined to be 0.19 mmol/g. The PI.Mo catalyst was activated using TSHP(5 mmol)/toluene for a period, and epoxidation of cyclohexene was carried out analogously as in Example 3, with an exception that the reaction was carried out at a temperature of 80° C. employing the activated PI.Mo catalyst. Then, the yields of cyclohexene oxide(%) depending on the degree of activation of the catalyst and reaction time were determined, which were disclosed in Table 1 below.

TABLE 11

The yield of cyclohexene oxide produced by the epoxidation of cyclohexene depending on the degree of activation of a catalyst (unit: %)

| Reaction time (min) | Nonactivated | Activated for 12 hrs | Activated for 24 hrs | Activated for 48 hrs |
|---|---|---|---|---|
| 20 | 100 | 94.4 | 87.1 | 94.4 |
| 40 | 100 | 100 | 100 | 100 |
| 60 | 100 | 100 | 100 | 100 |
| 80 | 100 | 100 | 100 | 100 |
| 100 | 100 | 100 | 100 | 100 |
| 120 | 100 | 100 | 100 | 100 |

EXAMPLE 11

The stability of the PI.Mo catalyst was investigated in an analogous manner as in Example 4. The yields of cyclohexene oxide(%) produced by the epoxidation of cyclohexene using the catalysts activated for 0, 12, 24 and 48 hrs were determined, which were disclosed in Tables 12, 13, 14 and 15 below, respectively.

While U.S. Pat. No. 5,420,313 teaches that the stability of a Mo catalyst impregnated in polybenzimidazole, a heat-resistant polymer, increases as the activation time in the epoxidation of cyclohexene is longer, the PI.Mo catalyst prepared in the invention showed the best stability when it was not activated. Further, once the catalyst was activated, its stability increased depending on the activation time.

TABLE 12

The yield of cyclohexene oxide produced by the epoxidation of cyclohexene using a nonactivated PI.Mo catalyst (unit: %)

| Experiment No. | Reaction time | | | |
|---|---|---|---|---|
| | 20 min | 40 min | 60 min | 80 min |
| 1 | 100 | 100 | 100 | 100 |
| 2 | 96.6 | 100 | 100 | 100 |
| 3 | 93.9 | 100 | 100 | 100 |
| 4 | 90.5 | 100 | 100 | 100 |
| 5 | 82.1 | 100 | 100 | 100 |
| 6 | 67.8 | 100 | 100 | 100 |
| 7 | 52.9 | 92.3 | 100 | 100 |
| 8 | 43.8 | 86.4 | 100 | 100 |
| 9 | 23.9 | 82.7 | 100 | 100 |
| 10 | 9.4 | 65.3 | 89.4 | 100 |

TABLE 13

The yield of cyclohexene oxide produced by the epoxidation of cyclohexane using a PI.Mo catalyst activated for 12 hrs (unit: %)

| Experiment No. | Reaction time | | | | | |
|---|---|---|---|---|---|---|
| | 20 min | 40 min | 60 min | 80 min | 100 min | 120 min |
| 1 | 94.4 | 100 | 100 | 100 | 100 | 100 |
| 2 | 96.2 | 100 | 100 | 100 | 100 | 100 |
| 3 | 90.7 | 100 | 100 | 100 | 100 | 100 |
| 4 | 79.1 | 100 | 100 | 100 | 100 | 100 |
| 5 | 55.3 | 87.8 | 100 | 100 | 100 | 100 |
| 6 | 35.0 | 62.8 | 81.4 | 91.5 | 100 | 100 |
| 7 | 19.8 | 33.6 | 55.1 | 74.6 | 86.5 | 95.9 |
| 8 | 8.3 | 11.7 | 16.6 | 35.3 | 59.4 | 77.9 |
| 9 | 4.8 | 6.3 | 7.4 | 8.9 | 30.5 | 52.9 |
| 10 | 4.5 | 7.6 | 16.4 | 25.7 | 32.3 | 44.0 |

TABLE 14

The yield of cyclohexene oxide produced by the epoxidation of cyclohexene using a PI.Mo catalyst activated for 24 hrs (unit: %)

| Experiment No. | Reaction time | | | | | |
|---|---|---|---|---|---|---|
| | 20 min | 40 min | 60 min | 80 min | 100 min | 120 min |
| 1 | 87.1 | 100 | 100 | 100 | 100 | 100 |
| 2 | 92.0 | 100 | 100 | 100 | 100 | 100 |
| 3 | 78.1 | 100 | 100 | 100 | 100 | 100 |
| 4 | 37.2 | 83.6 | 100 | 100 | 100 | 100 |
| 5 | 21.1 | 62.1 | 88.7 | 100 | 100 | 100 |
| 6 | 16.3 | 50.4 | 82.3 | 94.2 | 100 | 100 |
| 7 | 7.2 | 13.7 | 40.4 | 67.6 | 82.3 | 91.0 |
| 8 | 6.8 | 13.8 | 37.0 | 61.7 | 78.5 | 92.0 |
| 9 | 6.1 | 8.9 | 23.1 | 43.6 | 64.8 | 77.4 |
| 10 | 4.9 | 7.8 | 15.0 | 35.6 | 54.6 | 67.8 |

TABLE 15

The yield of cyclohexene oxide produced by the epoxidation of cyclohexene using a PI.Mo catalyst activated for 48 hrs (unit: %)

| Experiment No. | Reaction time | | | | | |
|---|---|---|---|---|---|---|
| | 20 min | 40 min | 60 min | 80 min | 100 min | 120 min |
| 1 | 94.4 | 100 | 100 | 100 | 100 | 100 |
| 2 | 93.6 | 100 | 100 | 100 | 100 | 100 |
| 3 | 80.0 | 100 | 100 | 100 | 100 | 100 |
| 4 | 60.6 | 93.7 | 100 | 100 | 100 | 100 |
| 5 | 45.1 | 81.2 | 98.2 | 100 | 100 | 100 |
| 6 | 31.0 | 66.5 | 86.0 | 100 | 100 | 100 |
| 7 | 13.9 | 32.1 | 63.8 | 83.4 | 93.0 | 100 |
| 8 | 11.6 | 25.9 | 56.1 | 76.0 | 87.4 | 92.3 |
| 9 | 8.6 | 13.0 | 36.9 | 63.4 | 74.5 | 84.7 |
| 10 | 8.3 | 9.6 | 26.3 | 52.6 | 70.0 | 80.4 |

EXAMPLE 12

Epoxidation of cyclohexene using the non-activated PI.Mo catalyst were carried out at various temperatures of 60° C., 70° C. and 80° C., in an analogous manner as in Example 3. Then, the yields of cyclohexene oxide(%) produced by the epoxidation of cyclohexene were determined, which were disclosed in Table 16 below.

TABLE 16

The yield of cyclohexene oxide produced by the epoxidation of cyclohexene depending on the reaction temperature (unit: %)

| Reaction time (min) | Reaction temperature | | |
|---|---|---|---|
| | 60° C. | 70° C. | 80° C. |
| 20 | 74.0 | 93.6 | 100 |
| 40 | 91.5 | 100 | 100 |
| 60 | 97.7 | 100 | 100 |
| 80 | 100 | 100 | 100 |
| 100 | 100 | 100 | 100 |
| 120 | 100 | 100 | 100 |

On the other hand, 10 times of epoxidation of cyclohexene using the non-activated PI.Mo catalyst were carried out at 60° C. and 70° C., respectively, in an analogous manner as in Example 4. Then, the yields of cyclohexene oxide(%) produced epoxidation of cyclohexene were determined, which were disclosed in Tables 17 and 18 below.

TABLE 17

The yield of cyclohexene oxide produced by the epoxidation of cyclohexene using a nonactivated PI.Mo catalyst at 60° C. (unit: %)

| Experiment No. | Reaction time | | | | | |
|---|---|---|---|---|---|---|
| | 20 min | 40 min | 60 min | 80 min | 100 min | 120 min |
| 1 | 74.0 | 91.5 | 97.9 | 100 | 100 | 100 |
| 2 | 57.6 | 87.8 | 97.6 | 100 | 100 | 100 |
| 3 | 42.7 | 73.0 | 89.3 | 90.1 | 100 | 100 |
| 4 | 42.1 | 71.0 | 88.0 | 95.8 | 100 | 100 |
| 5 | 21.4 | 50.1 | 83.7 | 94.5 | 97.3 | 100 |
| 6 | 36.0 | 63.0 | 75.9 | 86.0 | 92.0 | 96.9 |
| 7 | 19.9 | 42.1 | 57.9 | 69.0 | 78.3 | 85.7 |
| 8 | 14.7 | 30.1 | 44.8 | 57.0 | 67.0 | 74.4 |
| 9 | 9.5 | 21.0 | 31.9 | 41.9 | 50.0 | 58.9 |
| 10 | 5.5 | 12.8 | 20.3 | 28.1 | 33.8 | 40.8 |

TABLE 18

The yield of cyclohexene oxide produced by the epoxidation of cyclohexene using a nonactivated PI.Mo catalyst at 70° C. (unit: %)

| Experiment No. | Reaction time | | | | | |
|---|---|---|---|---|---|---|
| | 20 min | 40 min | 60 min | 80 min | 100 min | 120 min |
| 1 | 93.0 | 100 | 100 | 100 | 100 | 100 |
| 2 | 85.8 | 100 | 100 | 100 | 100 | 100 |
| 3 | 84.3 | 100 | 100 | 100 | 100 | 100 |
| 4 | 77.2 | 100 | 100 | 100 | 100 | 100 |
| 5 | 63.6 | 92.2 | 100 | 100 | 100 | 100 |
| 6 | 55.6 | 96.6 | 100 | 100 | 100 | 100 |
| 7 | 47.5 | 77.9 | 93.6 | 100 | 100 | 100 |
| 8 | 39.8 | 70.9 | 86.6 | 94.4 | 100 | 100 |
| 9 | 27.2 | 57.4 | 74.2 | 88.9 | 96.2 | 100 |
| 10 | 21.8 | 47.9 | 69.5 | 84.5 | 93.0 | 100 |

EXAMPLE 13

Epoxidation of cyclohexene was carried out by employing the non-activated PI.Mo catalyst prepared in Example 10 analogously as in Example 8, with an exception that cumene hydroperoxide was employed as an oxygen-donating agent instead of tert-butyl-hydroperoxide and the composition of reaction mixture was as below:

| cyclohexene | 74 mmol |
|---|---|
| Mo | $1.52 \times 10^{-2}$ mmol |
| cumene hydroperoxide | 5 mmol |
| ortho-dichlorobenzene | 0.5 ml |

Then, the yields of cyclohexene oxide(%) produced by the epoxidation of cyclohexene were determined, which were disclosed in Table 19 below. As can be seen in Table 19, it was found that the non-activated PI.Mo catalyst showed excellent selectivity and stability.

TABLE 19

The yield of cyclohexene oxide produced by the epoxidation of cyclohexene using a nonactivated PI.Mo catalyst (unit: %)

| Experiment No. | Reaction time | | | | | |
|---|---|---|---|---|---|---|
| | 20 min | 40 min | 60 min | 80 min | 100 min | 120 min |
| 1 | 90.0 | 100 | 100 | 100 | 100 | 100 |
| 2 | 88.4 | 100 | 100 | 100 | 100 | 100 |
| 3 | 85.0 | 100 | 100 | 100 | 100 | 100 |
| 4 | 82.7 | 100 | 100 | 100 | 100 | 100 |
| 5 | 69.7 | 100 | 100 | 100 | 100 | 100 |
| 6 | 69.4 | 100 | 100 | 100 | 100 | 100 |
| 7 | 68.7 | 90.3 | 100 | 100 | 100 | 100 |
| 8 | 39.1 | 78.5 | 90.8 | 100 | 100 | 100 |
| 9 | 31.9 | 76.3 | 93.6 | 100 | 100 | 100 |
| 10 | 26.2 | 59.4 | 79.9 | 94.1 | 100 | 100 |

EXAMPLE 14

Epoxidation of Cyclooctene

Epoxidation of cis-cyclooctene using the non-activated PI.Mo catalyst was carried out analogously as in Example 8, with an exception that the composition of reaction mixture was as below:

| cis-cycloctene | 57.6 mmol |
|---|---|
| Mo | $1.52 \times 10^{-2}$ mmol |
| tert-butyl-hydroperoxide | 5 ml |
| ortho-dichlorobenzene | 0.5 mmol |
| toluene | 0.62 ml |

Then, the yields of cyclooctene oxide(%) produced by the epoxidation of cyclooctene were determined, which were disclosed in Table 20 below.

TABLE 20

The yield of cyclohexene oxide produced by the epoxidation of cyclohexene using a nonactivated PI.Mo catalyst (unit: %)

| Experiment No. | reaction time | | | |
|---|---|---|---|---|
| | 20 min | 40 min | 60 min | 80 min |
| 1 | 56.9 | 76.1 | 100 | 100 |
| 2 | 88.5 | 95.2 | 100 | 100 |
| 3 | 87.6 | 94.6 | 100 | 100 |
| 4 | 89.6 | 94.3 | 100 | 100 |
| 5 | 85.6 | 91.6 | 100 | 100 |
| 6 | 87.6 | 95.6 | 100 | 100 |
| 7 | 88.2 | 92.7 | 100 | 100 |
| 8 | 70.6 | 82.6 | 100 | 100 |
| 9 | 75.3 | 85.9 | 80.0 | 100 |
| 10 | 73.9 | 80.6 | 100 | 100 |

EXAMPLE 15

Epoxidation of styrene using the non-activated Pl.Mo catalyst was carried out analogously as in Example 8, with an exception that the composition of reaction mixture was as below:

| | |
|---|---|
| styrene | 65.5 mmol |
| Mo | $1.52 \times 10^{-2}$ mmol |
| ortho-dichlorobenzene | 0.5 ml |
| toluene | 0.62 ml |

Then, the yields of styrene oxide(%) produced by the epoxidation of styrene were determined, which were disclosed in Table 21 below.

TABLE 21

The yield of styrene oxide produced by the epoxidation of styrene using a nonactivated Pl.Mo catalyst (unit: %)

| Experiment No. | Reaction time | | | | | |
|---|---|---|---|---|---|---|
| | 20 min | 40 min | 60 min | 80 min | 100 min | 120 min |
| 1 | 45.0 | 62.5 | 70.1 | 71.6 | 73.5 | 73.9 |
| 2 | 47.3 | 68.2 | 82.3 | 87.3 | 96.2 | 100 |
| 3 | 25.0 | 45.6 | 65.9 | 75.0 | 86.1 | 98.7 |
| 4 | 22.0 | 43.0 | 61.3 | 69.0 | 78.6 | 89.0 |
| 5 | 19.9 | 37.6 | 52.6 | 60.3 | 77.1 | 85.4 |
| 6 | 17.3 | 29.3 | 45.3 | 55.0 | 70.5 | 75.0 |
| 7 | 17.0 | 28.6 | 44.3 | 54.9 | 69.2 | 75.2 |
| 8 | 15.1 | 26.0 | 42.1 | 46.8 | 52.0 | 58.1 |
| 9 | 5.6 | 13.6 | 24.2 | 39.3 | 36.5 | 46.1 |
| 10 | 5.0 | 11.0 | 19.6 | 33.8 | 36.9 | 38.2 |

EXAMPLE 16

Epoxidation of 1-Octene

Epoxidation of 1-octene using the non-activated Pl.Mo catalyst was carried out analogously as in Example 8, with an exception that the composition of reaction mixture was as below:

| | |
|---|---|
| 1-octene | 47.8 mmol |
| Mo | $1.52 \times 10^{-2}$ mmol |
| tert-butyl-hydroperoxide | 5 mmol |
| ortho-dichlorobenzene | 0.5 ml |
| toluene | 0.62 ml |

Then, the yields of 1,2-epoxy octene oxide(%) produced by the epoxidation of 1-octene were determined, which were disclosed in Table 22 below.

TABLE 22

The yield of 1,2-epoxy octene oxide produced by the epoxidation of 1-octene using a nonactivated Pl.Mo catalyst (unit: %)

| Experiment No. | Reaction time | | | | | |
|---|---|---|---|---|---|---|
| | 20 min | 40 min | 60 min | 80 min | 100 min | 120 min |
| 1 | 37.0 | 60.6 | 72.8 | 78.9 | 83.7 | 86.9 |
| 2 | 27.8 | 46.6 | 63.2 | 73.1 | 80.3 | 82.7 |
| 3 | 12.4 | 35.3 | 51.3 | 63.0 | 71.7 | 77.7 |
| 4 | 10.0 | 33.5 | 45.3 | 57.5 | 68.2 | 75.0 |
| 5 | 6.0 | 18.4 | 32.7 | 44.5 | 53.5 | 61.5 |
| 6 | 0 | 6.6 | 14.3 | 24.1 | 33.5 | 42.3 |
| 7 | 3.0 | 5.1 | 9.4 | 13.7 | 19.0 | 23.7 |
| 8 | 0 | 4.8 | 8.1 | 11.9 | 16.0 | 19.1 |
| 9 | 0 | 4.4 | 7.1 | 9.7 | 12.7 | 15.9 |
| 10 | 0 | 0 | 4.3 | 7.2 | 8.8 | 11.2 |

EXAMPLE 17

Epoxidation of 1-octene was carried out analogously as in Example 16 except for employing cumene hydroperoxide as an oxygen-donating agent instead of tert-butyl-hydroperoxide. Then, yields of 1,2-epoxy octene oxide(%) produced by the epoxidation of 1-octene were determined, which were disclosed in Table 23 below.

TABLE 23

The yield of 1,2-epoxy octene oxide produced by the epoxidation of 1-octene using a nonactivated Pl.Mo catalyst (unit: %)

| Experiment No. | Reaction time | | | | | |
|---|---|---|---|---|---|---|
| | 20 min | 40 min | 60 min | 80 min | 100 min | 120 min |
| 1 | 11.3 | 28.0 | 39.2 | 49.4 | 56.1 | 62.8 |
| 2 | 14.5 | 33.3 | 42.5 | 53.7 | 61.1 | 71.2 |
| 3 | 10.9 | 23.4 | 34.1 | 45.5 | 54.5 | 63.4 |
| 4 | 9.5 | 19.8 | 30.7 | 40.9 | 51.5 | 58.9 |
| 5 | 7.9 | 15.4 | 24.6 | 33.9 | 40.9 | 51.6 |
| 6 | 7.0 | 13.8 | 23.1 | 30.4 | 47.9 | 50.0 |
| 7 | 5.3 | 13.0 | 19.1 | 28.0 | 34.2 | 46.2 |
| 8 | 0 | 10.7 | 17.3 | 25.0 | 33.2 | 48.9 |
| 9 | 0 | 7.3 | 12.4 | 17.6 | 23.5 | 28.3 |
| 10 | 0 | 4.6 | 9.8 | 13.9 | 17.1 | 21.5 |

COMPARATIVE EXAMPLE

Epoxidation of 1-octene was carried out at 80° C.) by employing a homogenous catalyst of $MoO_2(acac)_2$, where tert-hydroperoxide or cumene hydroperoxide was used as an oxygen-donating agent. Then, the yields of 1,2-epoxy octene oxide(%) produced by the epoxidation of 1-octene were determined, which were disclosed in Tables 24 and 25 below.

TABLE 24

The yield of 1,2-epoxy octene oxide produced by the epoxidation of 1-octene using a homogenous catalyst of $MoO_2(acac)_2$, in case of employing TBHP as an oxygen-donating agent (unit: %)

| Reaction time (min) | Yield of 1,2-epoxy octene (%) |
|---|---|
| 20 | 82.4 |
| 40 | 90.9 |
| 60 | 95.1 |
| 80 | 97.2 |
| 100 | 98.6 |
| 120 | 100 |

TABLE 25

The yield of 1,2-epoxy octene oxide produced by the epoxidation of 1-octene using a homogenous catalyst of $MoO_2(acac)_2$, in case of employing cumene hydroperoxide as an oxygen-donating agent (unit: %)

| Reaction time (min) | Yield of 1,2-epoxy octene (%) |
|---|---|
| 20 | 55.4 |
| 40 | 67.2 |
| 60 | 76.6 |
| 80 | 79.4 |
| 100 | 83.2 |
| 120 | 100 |

EXAMPLE 18

Preparation of a V Catalyst Impregnated in Functional Group-Free Polyimide Resin To obtain a vanadium catalyst impregnated in polyimide resin(PI.V), a functional group-free polyimide obtained in Example 1-1 was impregnated with $VO(acac)_2$ catalyst. The V content in the PI.V catalyst was determined to be 0.12 mmol/g. Epoxidation of cyclohexene was carried out five times analogously as in Example 3 except for employing the recyclable PI.V catalyst. Then, the yields of cyclohexene oxide(%) produced by the epoxidation of cyclohexene were determined, which were disclosed in Table 26 below.

TABLE 26

The yield of cyclohexene oxide produced by the epoxidation of cyclohexene using a PI.V catalyst (unit: %)

| Reaction time (min) | Experiment No. 1 | Experiment No. 2 | Experiment No. 3 | Experiment No. 4 | Experiment No. 5 |
|---|---|---|---|---|---|
| 20 | 42.0 | 20.7 | 6.3 | 19.2 | 6.4 |
| 40 | 50.0 | 29.2 | 7.6 | 26.2 | 7.0 |
| 60 | 52.0 | 35.1 | 10.6 | 29.4 | 7.9 |
| 100 | 60.0 | 42.2 | 15.6 | 35.0 | 8.3 |
| 120 | 62.0 | 46.1 | 19.7 | 40.5 | 11.3 |
| 180 | 71.0 | 55.0 | 26.2 | 44.0 | 13.5 |
| 240 | 76.0 | 60.8 | 32.8 | 49.1 | 10.6 |
| 300 | 78.0 | 65.8 | 36.3 | 52.3 | 13.7 |
| 360 | 80.1 | 69.6 | 40.5 | 56.0 | 14.9 |
| 420 | 83.0 | 73.0 | 52.0 | 59.4 | 16.6 |

As clearly illustrated and demonstrated in the above, a heterogenous polyimide-supported transition metal complex catalyst of the invention can be prepared in a simple and economical manner. The catalyst of the invention, provides superior catalytic activity, selectivity and stability in the epoxidation of higher olefin. Further, the catalyst of the invention has strong resistance against heat and acid. Besides, the catalyst of the invention may provide the following advantages which are critical in industrial use: it permits relatively high yield of epoxy compounds; and, it can be easily isolated from the reaction product, which eases recycling of the catalyst.

What is claimed is:

1. A process for preparing epoxy compound from olefin, which comprises the steps of:

preparing a polyimide resin particle by condensation polymerization of dianhydride and diamine;

impregnating the polyimide resin particle with a homogeneous organic metal complex catalyst comprising one or more transition metals selected from the group consisting of molybdenum, vanadium, tungsten and titanium to give a heterogeneous polyimide-supported transition metal complex catalyst; and, reacting peroxide and olefin compound in a molar ratio of 1:0.5 to 1:100 in the presence of the heterogeneous polyimide-supported transition metal complex catalyst.

2. The process for preparing epoxy compound from olefin of claim 1, wherein the olefin compound is one or more selected from the group consisting of ethylene, propylene, butene, pentene, hexene, octene, decene, cyclohexene, 4-vinyl-cyclohexene, unsaturated glycerin ester, aryl chloride, aryl alcohol, styrene, methylene hexane, cyclopentadiene and butadiene.

3. The process for preparing epoxy compound from olefin of claim 2, wherein the olefin compound is one or more selected from the group consisting of propylene, 1-octene, 1-decene, cyclohexene, 4-vinyl-cyclohexene, aryl chloride and styrene.

4. The process for preparing epoxy compound from olefin of claim 1, wherein the peroxide is one or more selected from the group consisting of hydrogen peroxide, organic peroxide, peroxide ether and peracid.

5. The process for preparing epoxy compound from olefin of claim 4, wherein the peroxide is one or more selected from the group consisting of tert-butyl hydroperoxide, cumene hydroperoxide, ethylbenzene hydroperoxide and hydrogen peroxide.

6. The process for preparing epoxy compound from olefin of claim 1, wherein the peroxide and olefin compound is added in a molar ratio of 1:1 to 1:50, and reacted together in the presence of the catalyst whose molar ratio to the peroxide is 0.002:1 to 0.03:1.

7. The process for preparing epoxy compound from olefin of claim 1, wherein the molar ratio of the heterogeneous polyimide-supported transition metal complex catalyst to peroxide is controlled at a range of 0.00001:1 to 1:1.

8. The process for preparing epoxy compound from olefin of claim 1, wherein the polyimide resin particle comprises a main chain and functional groups which are involved in chemical bonds with the transition metals.

9. The process for preparing epoxy compound from olefin of claim 8, wherein the functional group is one selected from the group consisting of triazol, carboxyl, sulfonyl, pyridine, and hydroxyl.

10. The process for preparing epoxy compound from olefin of claim 1, wherein the heterogeneous polyimide-supported transition metal complex catalyst comprises 0.1 to 4 mmol/g of functional group of polyimide and 0.1 to 5 mmol/g of transition metal in a molar ratio of 1:1 to 15:1.

11. The process for preparing epoxy compound from olefin of claim 1, wherein the heterogeneous polyimide-supported transition metal complex catalyst comprises 0.25 to 2.5 mmol/g of functional group of polyimide and 0.1 to 2 mmol/g of transition metal in a molar ratio of 1:1 to 10:1.

* * * * *